(12) United States Patent
Deane et al.

(10) Patent No.: US 6,340,243 B1
(45) Date of Patent: Jan. 22, 2002

(54) LIQUID/GAS PHASE DETECTOR SYSTEM

(75) Inventors: Robert A. Deane, Encinitas; Jeffrey P. Deane, Carlsbad, both of CA (US)

(73) Assignee: Fluid Components Intl, San Diego, CA (US)

(*) Notice: Subject to any disclaimer, the term of this patent is extended or adjusted under 35 U.S.C. 154(b) by 0 days.

(21) Appl. No.: 09/205,524

(22) Filed: Dec. 3, 1998

(51) Int. Cl.⁷ .................... G01N 33/00; G01N 11/02; G01N 25/00; G01F 1/36
(52) U.S. Cl. ................ 374/24; 73/61.78; 73/204.21; 73/215
(58) Field of Search .................. 374/24; 73/204.21, 73/53.01, 215, 216, 61.76, 61.78, 19.1, 64.44, 861

(56) References Cited

U.S. PATENT DOCUMENTS

| | | | | |
|---|---|---|---|---|
| 3,366,942 A | * | 1/1968 | Deane ................. | 73/204.11 X |
| 3,874,223 A | * | 4/1975 | Miyazaki et al. .......... | 73/53.01 |
| 3,985,623 A | * | 10/1976 | Morgan et al. ........... | 73/215 X |
| 4,011,070 A | * | 3/1977 | Hynd ...................... | 65/341 X |
| 4,145,926 A | * | 3/1979 | Martig, Jr. ............... | 73/215 X |
| 4,195,520 A | * | 4/1980 | Shaver ................... | 73/215 |
| 4,571,997 A | * | 2/1986 | Kepple et al. ............ | 73/215 |
| 4,899,584 A | * | 2/1990 | McQueen ............... | 73/204.21 |
| 5,688,096 A | * | 11/1997 | Atkins ................... | 405/128 |

FOREIGN PATENT DOCUMENTS

| | | | | |
|---|---|---|---|---|
| GB | 2222961 A | * | 3/1990 | |
| JP | 53-22463 | * | 3/1978 | ............... 73/215 |
| JP | 60-35219 | * | 2/1985 | ............... 73/215 |
| JP | 1-173830 | * | 7/1989 | ............... 73/215 |

* cited by examiner

Primary Examiner—Thomas P. Noland
(74) Attorney, Agent, or Firm—The Maxham Firm

(57) ABSTRACT

A liquid/gas phase detector system employing a sensor to detect fluid phase, flow rate, and temperature. A flow conditioner in the form of a pipe segment with an inverted V-shaped section forming a weir is adapted for coupling in a horizontal conduit downstream from a source of liquid flow. When a thermal dispersion technology sensor is used, heated and non-heated temperature sensitive elements extend within the pipe segment on the upstream side of the weir. Fluid flow changes encountering the sensing elements cause temperature changes which produce an output signal relating to fluid phase (gas or liquid) and flow rate. Several different embodiments for the flow conditioner are provided.

34 Claims, 4 Drawing Sheets

LIQUID/GAS PHASE DETECTOR SYSTEM

BACKGROUND

1. Field of the Invention

This invention relates generally to flow detection systems, and more specifically to a sensor-based device for detecting a liquid-to-gas or gas-to-liquid phase change of a flowing fluid, in addition to measuring the temperature of the fluid and sensing variations in the flow rate of the fluid.

2. Description of the Related Art

Many processes use a pumping system to transfer a liquid from one location to another. In general, a typical pumping system consists of a motor, a pump, a mechanism to couple the motor to the pump, and at least a simple controller such as an ON/OFF switch. Most pump designs require that the internal parts of the pump be completely wet, or "primed," and that liquid flow rates remain above some minimum threshold. These requirements usually ensure adequate lubrication and cooling of the pump parts. Loss of prime, or flow rate reductions below the minimum threshold, which may be due to cavitation, conduit leakage or blockage, can cause detrimental over-heating and premature failure of the pump as well as other parts of the pumping system. The size of the pumping system is usually directly related to its thermal failure acceleration factor and repair cost. In other words, the larger the pumping system, the quicker it might fail if deprived of sufficient liquid flow, and the more expensive it could be to repair or replace the damaged parts.

The artificial lift of crude oil from underground formations and the filling or emptying of liquid storage vessels or tank cars are common examples that rely upon the use of relatively large, costly pumping systems. In both cases, the ability to promptly detect a liquid-to-gas or gas-to-liquid phase change of the flowing fluid is crucial to the proper operation of the system. Prompt phase change detection is also critical for maintaining safe, efficient, and reliable pumping system operation. Furthermore, being able to determine whether the fluid flow rate is increasing or decreasing, particularly detecting complete liquid or gas stoppage, which could be due to blockage of the conduit, provides greater ability for process management and pump control.

Numerous attempts at providing protection and effective control for pumps have been made for the application examples cited above as well as others, but with significant limitations in their levels of success. Sensors or combinations of sensors have been used to measure the electrical or mechanical energy being delivered to the pump; to detect the presence or absence of liquid at the pump; and to monitor the liquid temperature, pressure and flow rate through the pump. The energy measuring methods are indirect, or inferred measurements and, consequently, can be inaccurate and unreliable. Among the other methods used, though some are direct, most are single parameter measurements. Single parameter measurements typically have not been sufficiently sensitive, fast or smart enough to detect the combination of effects that indicate the valid occurrence of a liquid-to-gas or a gas-to-liquid phase change.

There is a recognized need in many situations where fluids are moved or transferred, for a rugged, industrial device that can precisely detect a liquid-to-gas or a gas-to-liquid phase change while the fluid is flowing through a conduit such as a pipe.

SUMMARY OF THE INVENTION

A major purpose of the present invention is to provide a simple and effective means to precisely determine fluid flow characteristics by employing a combination of a flow conditioner, a sensor, and a controller. The liquid/gas phase detector system of the preferred embodiment of the invention has the purpose and ability to identify and monitor the flow of either a liquid or a gas, or a combination, through a conduit such as a pipe. In addition, the invention detects the phase of the flowing fluid, stoppage of flow of either gas or liquid, flow surges, changes in the fluid flow rate through the conduit, and even the fluid temperature.

In a preferred embodiment of the invention, the flow conditioner or pipe segment is preferably a relatively short length of pipe having a reverse bend or an inverted V-shaped section forming a dam, or weir, over which the liquid flows. This pipe segment is coupled in a horizontal conduit, usually downstream of the pumping system and upstream of a check valve (if one is used). The inlet and outlet ends of the pipe segment preferably are axially aligned, with the top, or crest, of the weir being above the centerline or axis of the inlet of the pipe segment, but below the top dead center of the inside surface of the inlet. The inside diameter of the pipe segment is substantially constant from one end through to the other. During normal operation a reservoir of liquid forms on the upstream side of the weir. A reference plane is defined by the surface of the reservoir when the liquid is at the crest of the weir. The reference plane is therefore above the centerline of the inlet and outlet ends of the pipe segment. Depending on the conduit configuration upstream of the pipe segment, the surface area of this reference plane and hence, the upstream ullage, could be relatively large. Even with the reservoir filled to the level of the reference plane, this upstream ullage allows gas to flow through the pipe segment.

Some applications might require that the height of the weir crest be slightly above the top dead center of the inside surface of the inlet. This would form a liquid seal or gas trap, and prevent gas from flowing through the pipe segment if there is stoppage of liquid flow while the reservoir remains filled to the level of the reference plane. Upstream ullage is thereby zero due to this gas trap and the surface area of the reference plane is small (approximately equal to $\pi/4D^2$, where D is the pipe segment inside diameter at that level).

A sensor is mounted in the pipe segment wall on the upstream side between the weir and the inlet end. The preferred sensor utilizes thermal dispersion technology. This sensor has the ability to detect the presence or absence of liquid flowing over the weir, and to monitor the variation of the flow rate of gas or liquid through the pipe segment. It can also provide the temperature and phase of the flowing fluid, that is, whether there is liquid or gas flowing.

The controller converts the raw output signal from the sensor into useful control signals and display values. In its simplest form, the controller consists of a few interconnected functional blocks. The major blocks, in addition to a power supply, are input and output signal conditioners, and a signal processor with display, input keypad, and a memory. The memory is used with the processor in order to store and retrieve the operational instructions of the controller as well as the factory and end-user setup and calibration parameters. The signal processor contains timers and counters that are used for the timing, accumulation, and sequencing of input and output events. Relay contacts, analog voltages or currents, status lamps, visual displays, digital interfaces, audio signals, or any combination thereof can be configured as the outputs of the controller.

Once the pipe segment is filled with liquid, additional liquid flow causes the reservoir to rise above the reference plane and liquid to flow over the weir. The sensor is positioned just above the reference plane and detects a gas-to-liquid phase change when wetted by the rising reservoir level. As increased liquid flow rates further raise the reservoir level, the sensor monitors the changing liquid flow rate. The height (or depth) of liquid above the crest of the weir is relative to the liquid flow rate. When liquid flow stops, the reservoir level quickly returns to the level of the reference plane. At that point the sensor is no longer wetted and it detects a liquid-to-gas phase change. A typical structure of the flow conditioner and sensor of the system is such that if gas is flowing through the pipe segment, the gas flow can be monitored even though there is no liquid flow.

The sensor of the system has a fast response time and can monitor very low gas or liquid flow rates. This sensitivity enables the sensor to detect flow surges caused by entrained gas "slugs." Further, the sensor has the ability to detect gas pressure changes.

A particular feature of the phase detector system of the invention is that mechanical dependability is assured because there are no moving fluid-wetted parts or orifices to fail or foul. Another feature is a high signal-to-noise ratio which enables clear indications of phase change, flow rate, and fluid temperatures, among others.

Alternative embodiments of the flow conditioner are disclosed for modified flow detection purposes. The principle of operation of all the flow conditioner embodiments is the same.

BRIEF DESCRIPTION OF THE DRAWING

The objects, advantages, and features of the invention will be more readily perceived from the following detailed description, when read in conjunction with the accompanying drawing, in which.

DETAILED DESCRIPTION OF THE PREFERRED EMBODIMENTS

Figure 1:
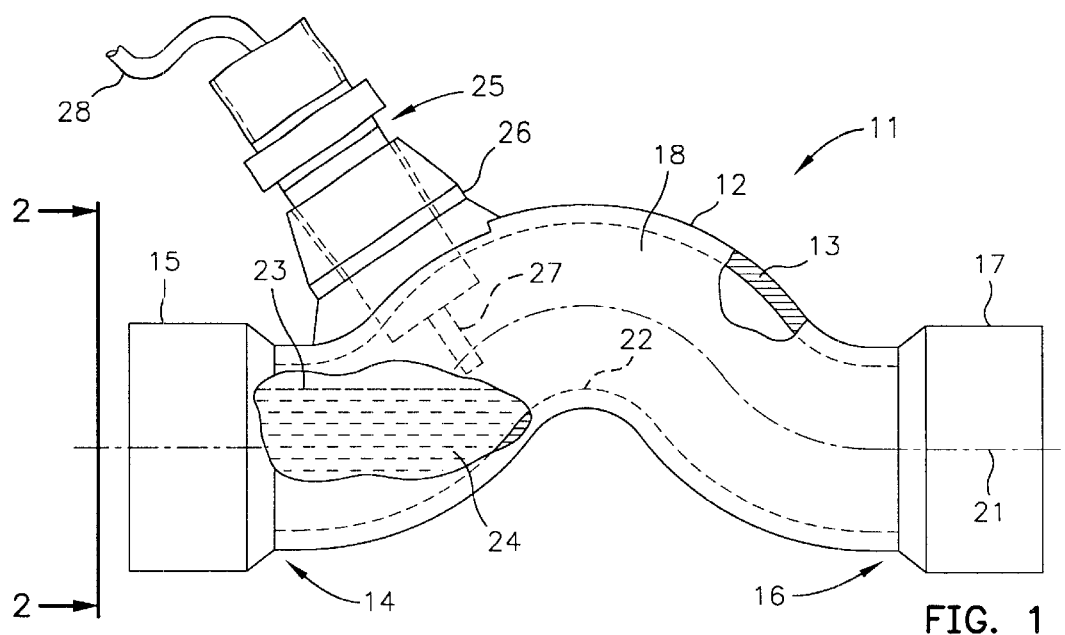
FIG. 1 is a partially cut away side view of the flow conditioner and sensor of the invention.

With reference now to the drawing and more particularly to FIG. 1 thereof, flow conditioner 11 is shown comprising pipe segment 12 having a reverse bend or a generally inverted V-shaped central portion. A section is broken away showing that the pipe has substantial thickness 13 and would normally be made of metal. However, any other suitable material with appropriate pressure rating and compatibility for the intended use would be satisfactory. Inlet end 14 is configured with an appropriate coupling or fitting 15 and outlet end 16 has a similar fitting 17. The centerline of the pipe segment is indicated by broken line 21. The axes of the inlet and outlet ends are intended to be substantially horizontally aligned, so that centerline 21 is on the same axis at both the inlet and outlet ends. The flow conditioner is intended to be installed horizontally in the orientation shown so that dam or weir 22 is above the level of centerline 21 at the inlet and outlet ends. The flow conditioner is preferably located upstream of the main check valve, if one is used, and downstream from the pump. Preferably the conduit has a downward turn within a few feet downstream from the outlet end of the flow conditioner. This downstream section of conduit acts as a gas accumulator and ensures that enough gas is available to fill the upper chamber, or gas trap 18, of the flow conditioner when liquid flow stops. Another portion of the flow conditioner is broken away showing the top surface 23 of liquid reservoir 24 in the inlet end. A reference plane is defined by surface 23 of the reservoir when the liquid is at the crest of weir 22.

Sensor 25 is connected through mounting hub 26 on the top of pipe segment 12 and on the upstream side of weir 22. Sensing element 27 extends generally downwardly into gas trap 18 toward, but short of, reservoir reference plane 23. Cable 28 of sensor 25 is coupled to the controller which will be discussed below.

Figure 2:
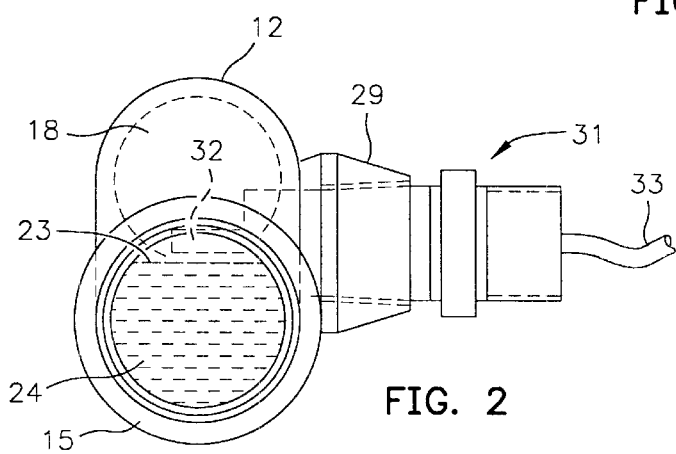
FIG. 2 is an end view of an alternative embodiment of the mounting of the sensor within the flow conditioner of the invention.

In an alternative embodiment, sensor 31 is mounted at the side of pipe segment 12 with mounting hub 29 as shown in FIG. 2. Sensing element 32 extends generally laterally into gas trap 18 of pipe segment 12 upstream from weir 22 and positioned slightly above reservoir reference plane 23. Cable 33 connects to the controller in this embodiment.

The pipe segment, inlet and outlet fittings, and sensor mounting hub may be welded together to form the flow conditioner of the phase detector system of the invention. Alternatively, the entire flow conditioner assembly could be a unitary molded or cast part.

For normal operation, one or more sensing elements 27 (as shown in FIG. 1) would be mounted through wall 13 of pipe segment 12 in a manner to, as precisely as possible, determine the flow characteristics of any fluid flowing through the pipe segment. In the preferred embodiment, sensing element 27 is part of a thermal dispersion type sensor which includes two sensing elements, one being the reference element which is always at ambient temperature and the other being a heated or active element. Use of a thermal dispersion sensor comprised of resistance temperature detectors (RTDs), which exhibit a change in resistance with temperature changes [R=f(T)], is preferred. Other temperature sensitive elements, such as thermistors or thermocouples, for example, could be used.

When there is no fluid flowing through pipe segment 12, there will be a large temperature differential, typically referred to as "delta-T" ($\Delta T$), between the two sensing elements. In this condition, the sensor exhibits a maximum $\Delta T$ between the reference and the heated sensing elements. When there is any kind of fluid flow, the heated element will be subject to heat dissipation caused by the fluid flow through the pipe segment. This heat dissipation causes a change in temperature of the heated element. With such fluid flow, the output from sensor 25 (in the FIG. 1 embodiment) will indicate a decrease in $\Delta T$ and the amount of temperature change of the heated element will indicate whether the fluid is gaseous or liquid. The amount of ΔT change also indicates the relative rate of fluid flow through the pipe segment.

The thermal dispersion sensing elements are strategically located slightly above the reservoir reference plane. This reservoir-to-sensor separation distance is important because the sensing elements must be close to the reference plane in order to allow for low flow detection of liquids, but not so close that wicking could occur due to the surface tension of the liquid under decreasing and no-flow conditions. A preferred distance above the reference plane for the bottom of the sensing elements is about 1/8 to about 3/16 inch. A thermal dispersion sensor is sufficiently sensitive to provide complete gas and liquid flow information. Detectable liquid flow velocities can be as low as 0.01 feet per second, and detectable gas flow velocities can be as low as 0.25 feet per second.

Even with the reservoir filled to the reference plane level, the preferred embodiment of the phase detector system of the invention allows for an inlet-to-outlet gas flow path. Because the sensing elements are located slightly above the reference plane of the reservoir, these elements are in the gas flow path. In this way, the sensor is able to detect the gas flow rate. In addition to the very low gas flow rate sensitivity that the thermal dispersion type of sensor provides, thermal technology also affords the ability to detect gas pressure changes. It is known that an increase in gas pressure causes an increase in gas density. Increased gas density causes an increase in heat dissipated by the heated element of a thermal dispersion sensor. This effect results in a decrease in ΔT which is directly related to pressure increases.

While physically intrusive elements, such as thermal sensors, are preferred because of their ability to measure multiple parameters, it is possible to employ other types of sensors, including non-intrusive ones, particularly sensors that can detect liquid level. These could include radio frequency (RF), ultrasonic, capacitive or inductive sensors, among others. The minimum sensor requirement is the ability to detect the presence or absence of a gas or liquid, that is, a dry or a wet condition at the weir.

Figure 3:
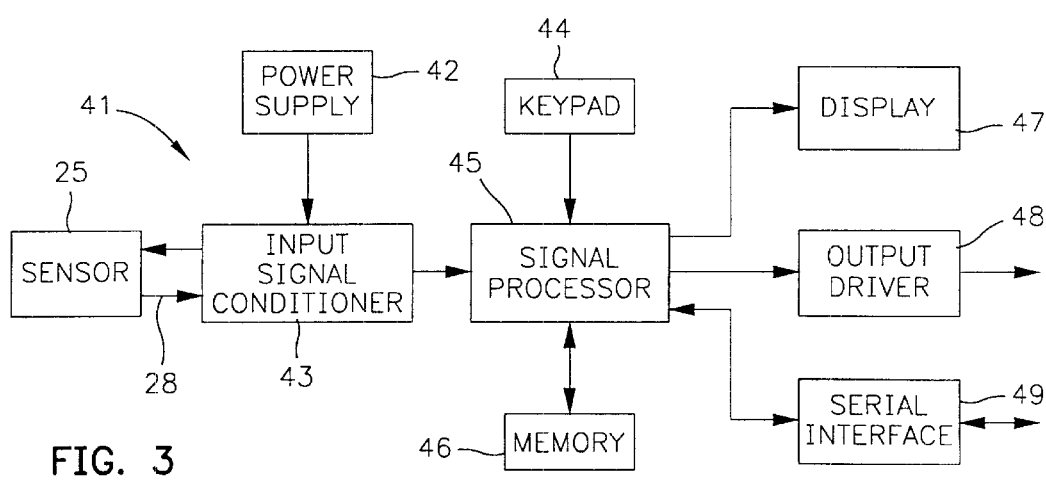
FIG. 3 is an example of a controller in block diagram form which may be used with the invention of FIG. 1 or FIG. 2.

The following discussion of the controller of FIG. 3 employs the term "sensor" in the general sense.

The signals from the sensor are applied to controller 41 which is shown in block diagram form in FIG. 3. The controller is the electronic circuit that converts the raw sensor signals into useful system information. Typically, the controller is configured and programmed for a given application.

The controller is powered by power supply 42. Sensor 25 (in the FIG. 1 embodiment) usually receives its power from the input signal conditioner 43 and, in turn, the raw output signals from the sensor are converted and scaled by the input signal conditioner. Keypad 44 is provided for entry of data and to instruct signal processor 45 as to the desired processing, the visual information shown on display 47, and the output setup. Memory 46 is provided to enable the storage and retrieval of operational instructions for the controller as well as the factory and end-user setup and calibration parameters. Output driver 48 and serial interface 49 are configured according to the application requirements and are driven by the signal processor.

The controller is capable of accepting analog or digital input signals and providing analog or digital output signals. The signal processor memory is partitioned into segments that contain the operating code of the controller (read-only memory), instrument-specific setup and calibration parameters (read and write memory with high-level write protection), and application-specific setup and calibration parameters (read and write memory with low-level write protection). Memory programming can be accomplished via either the keypad or the serial interface. The serial interface would normally be of a common format, such as RS-232 or RS-485, and can be connected to a motor controller, programmable logic controller (PLC), or distributed control system (DCS) as required by the specific application. The serial interface provides two-way communication between the controller of the phase detector system and whatever is connected to it.

Many display formats are possible. The display could be as simple as a single status lamp used to indicate liquid or gas phase at the sensor; or as meaningful as a continuous, real-time trace of the output signal of the sensor, showing specific time-correlated events (of the type of FIG. 4).

Figure 4:
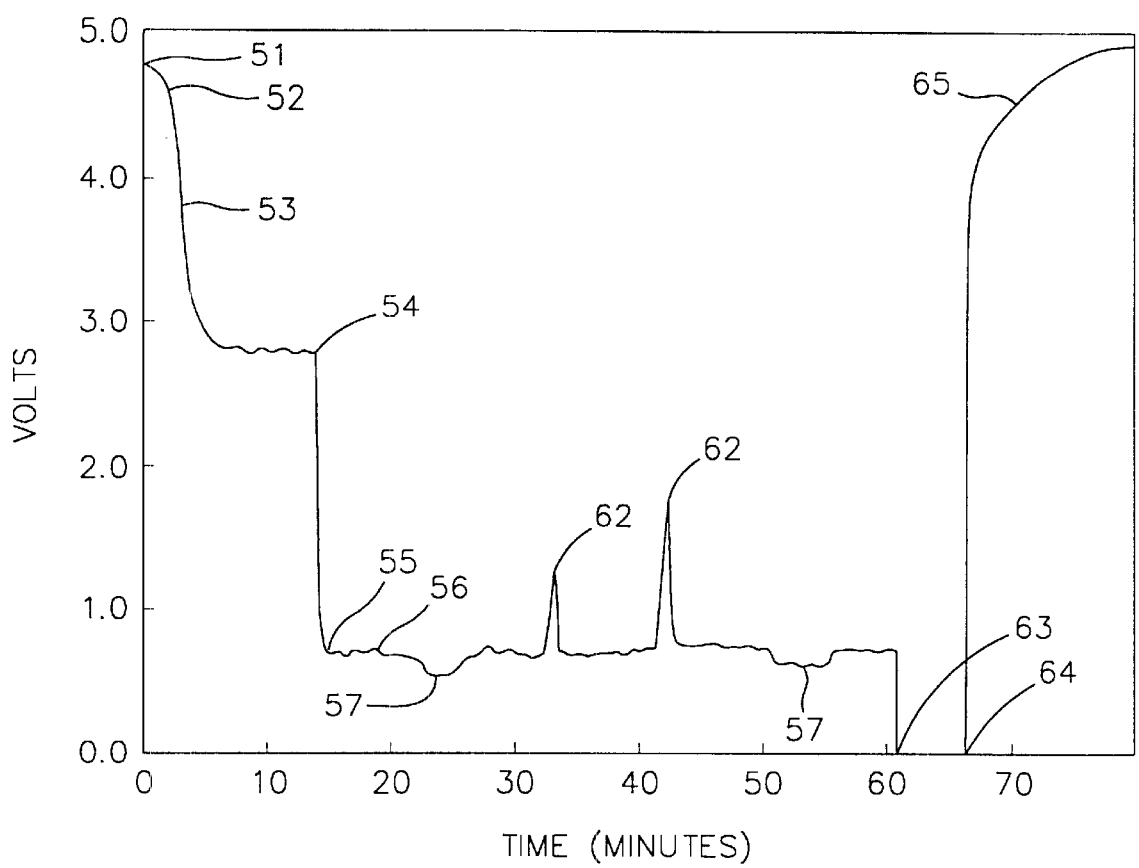
FIG. 4 is a plot of the sensor response signal of the system of the invention in volts vs. elapsed time when the system is connected to an operating oil well and under a variety of conditions.

With reference now to FIG. 4, which is a plot of output signal level (volts) versus time, there is shown an example of particular flow characteristics which could occur at a producing oil well, as detected by the preferred embodiment of the phase detector system of the invention. For this particular example, a down-hole progressive cavity pump is artificially lifting liquid from a 3700 foot deep well. The average daily well production is 105 barrels per day (BBL/day) gross-fluid, which could be comprised of 35 BBL/day of oil, 74 BBL/day of water, and 21,000 cubic feet per day (cfd) of gas. The flow conditioner of the invention is located closely downstream of the wellhead. The check valve for the well is located downstream of the flow conditioner and has a gathering system backpressure of 87 psig on it for this example.

FIG. 4 represents a trace of the output signal from the FIG. 3 block diagram over a period in excess of one hour after pump startup. In this example, prior to a startup, the pump had been at rest long enough to allow sufficient accumulation of liquid over the pump (LOP).

Any time the pump rests, liquid from the previous pump operation drains back down into the production tubing to some indeterminate level where it reaches a pressure equilibrium. Therefore, the sensor is dry, there is no flow of gas or liquid and the pressure is low, approximately atmospheric, or even at a slight vacuum. With no heat dissipation resulting from fluid flow, the ΔT of the sensor, and hence, the output voltage, is high, which is depicted at point 51 in FIG. 4.

Sensor Detects Gas Pressurization

As soon as the pump starts, liquid begins moving up the production tubing toward the wellhead, compressing the gas ahead of it and around sensing element 27 (in the FIG. 1 embodiment), showing at point 52 some slight increase in heat dissipation due to the gas pressurization. The sensor output voltage is inversely related to heat dissipation. In other words, an increase in heat dissipation is displayed as a decrease in output voltage. During this time the check valve of the well, which is downstream of the flow conditioner, remains closed because of the gathering system backpressure. The output voltage continues to drop toward point 53 because of the increased heat dissipation on sensing element 27 resulting only from the increasing pressure.

Sensor Detects Gas Flow

When the pressure upstream of the check valve (and at sensing element 27) slightly exceeds the gathering system backpressure, the check valve opens, allowing gas to flow. The output voltage reduction between points 53 and 54 reflects the response of the sensor to this gas flow. Both the flow rate and the pressure of the gas remain relatively constant as long as the rate of rise of the liquid in the production tubing is constant.

Sensor Detects Gas-To-Liquid Phase Change

Eventually the rising liquid reaches the wellhead and the flow conditioner, fills the reservoir, and begins to flow over the crest of the weir. Point 54 results from the initial liquid wetting of sensing element 27. As more liquid flows over the weir, the output voltage continues to reduce as the sensor reaches equilibrium based upon the amount of flowing liquid, and the output signal level reaches point 55.

Abnormalities Detected During Pump Startup

Although a typical "normal" pump startup is shown in FIG. 4, abnormal conditions can also be detected by the system of the invention. In particular, any output voltage increase occurring between points 51 and 55 would indicate a pump startup problem.

Sensor Detects Liquid Flow Rate Changes

As liquid continues to flow at a relatively steady rate, the generally flat portion 56 of the trace results. An increase in flow rate is reflected by dip 57 in the trace as more heat is dissipated from sensing element 27 and the output voltage drops farther. This is a typical response due to a periodic decrease in the gathering system backpressure.

Sensor Detects Gas Slugs In The Liquid Flow

Relatively discontinuous peaks or spikes 62 indicate that gas slugs are traveling past sensing element 27. This is a relatively normal occurrence for artificial lift. The reason that there are voltage spikes in conjunction with gas slugs is that the flowing gas dissipates much less heat than does the flowing liquid. These gas slugs can cause other types of controllers to assume a loss-of-flow condition and falsely shutdown the pump.

Sensor Detects Power Failure and Liquid-To-Gas Phase Change

Absolute discontinuity 63 indicates power failure and total shutdown of the pumping and phase detector system. When the power comes back on at 64, there is no flow and liquid has again drained down the production tubing, resulting in the output voltage immediately becoming high, as at 65. When the pump is restarted, the output signal should plot a trace that is similar to what is shown between points 51 and 55 if the startup is "normal."

It is believed that thermal dispersion is the best sensor technology currently available that enables a single device to be able to detect the flow rate of a liquid or a gas as well as the presence or absence of a liquid. This same technology also offers very low gas and liquid flow rate detection sensitivity, a wide dynamic flow rate monitoring range, fouling immunity, and the benefit of fluid temperature measurement without the addition of a separate sensor.

While the sensor is described above in the exemplary embodiment as comprising two temperature or RTD sensing elements, one unheated as a reference and the other being a heated sensor, other configurations are also possible. For example, a single sensing element operating on a time-share basis could be employed. In relatively rapid succession, a reference resistance reading is taken, then the sensor is heated and a heat dissipated resistance reading is taken. A comparison is then made to determine ΔT as described before, where simultaneous readings from two sensing elements were employed. Alternatively, the single sensing element could be held at a constant heated temperature. A measurement of the magnitude and rate-of-change of power required to maintain this constant temperature could then be used to determine fluid phase and flow rate.

In addition to the internally-heated thermal sensor configurations employing one or two sensing elements, a three-element sensor can be used. In this configuration, two elements comprise an adjacent pair of a heater and a temperature sensing element, while the third element is the unheated reference temperature sensing element. Examples of this type of flow detector are shown in U.S. Pat. Nos. 3,366,942 and 4,899,584. Thus, there are several configurations for employing thermal dispersion technology together with the reverse-bend pipe segment of this invention to obtain the fluid phase and flow rate indications desired.

For completeness, and with reference to the controller of FIG. 3, a brief discussion follows of how the RTD sensing element signals are handled for useful outputs. Two different methods may be used with a thermal dispersion sensor to determine the flow rate in a conduit. One is configured to maintain a constant temperature differential between the reference sensing element and the heated sensing element. This method measures the voltage, current, or power required to maintain the heated sensing element at a constant temperature above the reference sensing element while heat is removed by dissipation from the heated sensing element by way of the physical properties of the flowing fluid. The other method measures the temperature difference between the heated and the reference sensing elements while the heated sensing element is heated by a constant voltage, a constant current, or a constant power heat source. During this measurement, as with the other method, the heated sensing element loses heat by way of dissipation due to the physical properties of the flowing fluid.

Gas Accumulating Flow Conditioner

Figure 5A:
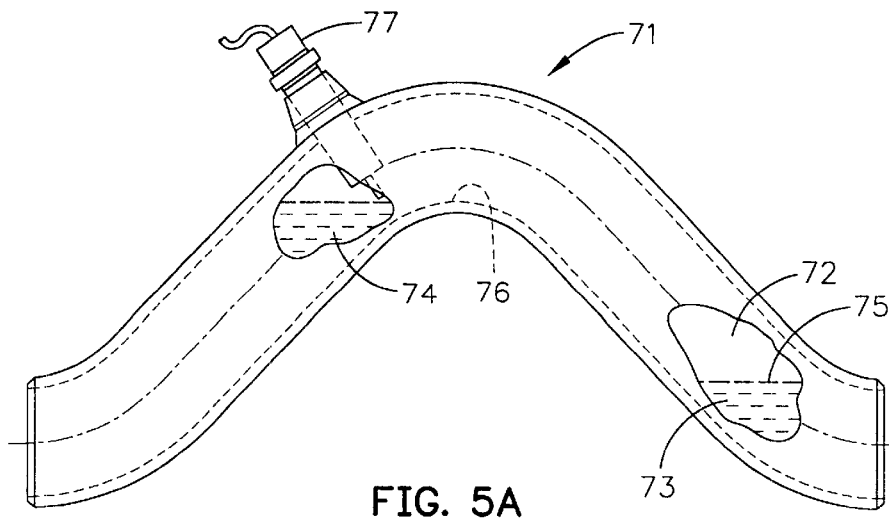
FIG. 5A is a side view of an alternative embodiment of the FIG. 1 flow conditioner.

The alternative flow conditioner configuration of FIG. 5A is particularly useful in installations where a downward conduit turn near the flow conditioner outlet is not available or possible. In this embodiment, the inlet and outlet are on the same centerline.

This flow conditioner configuration 71 shares attributes that are similar to the ones shown in FIGS. 1 and 2. Here, both arms of the inverted V-shaped pipe section are lengthened in order to increase the volume of gas trap 72. The gas trap volume is increased such that, regardless of the conduit configuration at the outlet of the flow conditioner, enough gas will always be accumulated and held within the trap to ensure that the sensing elements quickly "go dry" when the liquid flow stops. Sensor 77 is shown mounted in the same position as is sensor 25 in FIG. 1.

After initial startup and under normal operation, a secondary reservoir 73 will form at the flow conditioner outlet. This new reservoir forms in addition to primary reservoir 74, which is equivalent to reservoir 24 in FIG. 1. The height of surface 75 of secondary reservoir 73 will vary with the downstream conduit configuration, the liquid flow rate, and the static pressure within the flow conditioner. However, under no set of normal operation circumstances will the surface of the secondary reservoir ever be as high as the crest of the weir 76.

When liquid flow stops, gas flow rate monitoring isn't possible with this configuration because of the liquid seal or gas trap that is created by the reservoirs. This is based on the assumption that either or both reservoirs within the flow conditioner remain filled.

Figure 5B:
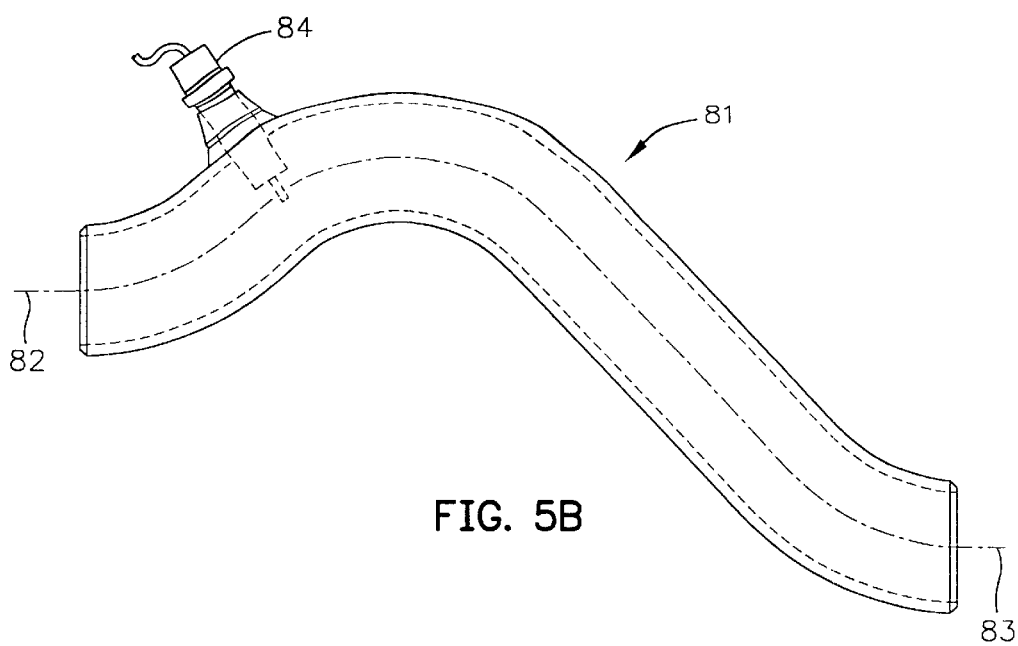
FIG. 5B is a side view of a modified embodiment of the flow conditioner of FIG. 5A.

Conditioner 81 of FIG. 5B functions substantially the same as the FIG. 5A embodiment. The only difference is that inlet centerline 82 is above outlet centerline 83. Thus, in this configuration, only the downstream arm of the inverted V-shaped pipe section is lengthened. Sensor 84 is also shown mounted in the same position as is sensor 25 in FIG. 1.

Velocity Reducing Flow Conditioner

Figure 6:
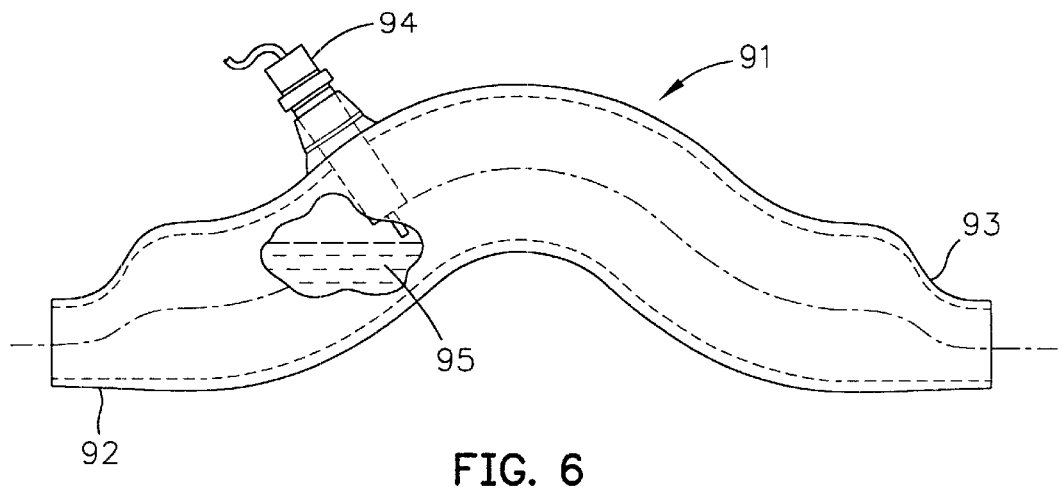
FIG. 6 is a side view of another alternative embodiment of the FIG. 1 flow conditioner, particularly for high flow rate installations.

In high flow rate installations it may be necessary to employ the FIG. 6 configuration of flow conditioner 91. This conditioner also shares attributes that are similar to the ones shown in FIGS. 1 and 2. In this case, the diameter of the inverted V-shaped pipe section is increased in order to reduce the liquid velocity at the sensor. Eccentric reducers 92 and 93 are used respectively at the inlet and outlet ends of the flow conditioner to couple it to the pumping system conduit. However, the outlet reducer is optional.

The velocity of the liquid at sensor 94 is proportional to the velocity of the liquid at the flow conditioner inlet times the ratio of the square of the inlet conduit inside diameter to the square of the conduit inside diameter at the sensor times an adjustment factor for the partially-filled condition at the sensor:

$$V_{at\ sensor} \approx V_{at\ inlet}[(ID_{at\ inlet})^2/(ID_{at\ sensor})^2]k.$$

The conduit diameter at the sensor is selected such that the liquid velocity at the sensor is within the measurement range of the sensing element.

When liquid flow stops, gas flow rate monitoring is not possible with this configuration either. This is because the eccentric reducer at the inlet of the flow conditioner creates a liquid seal or gas trap as long as primary reservoir 95 remains filled.

Combined Velocity Reducing And Gas Accumulating Flow Conditioner

Figure 7:
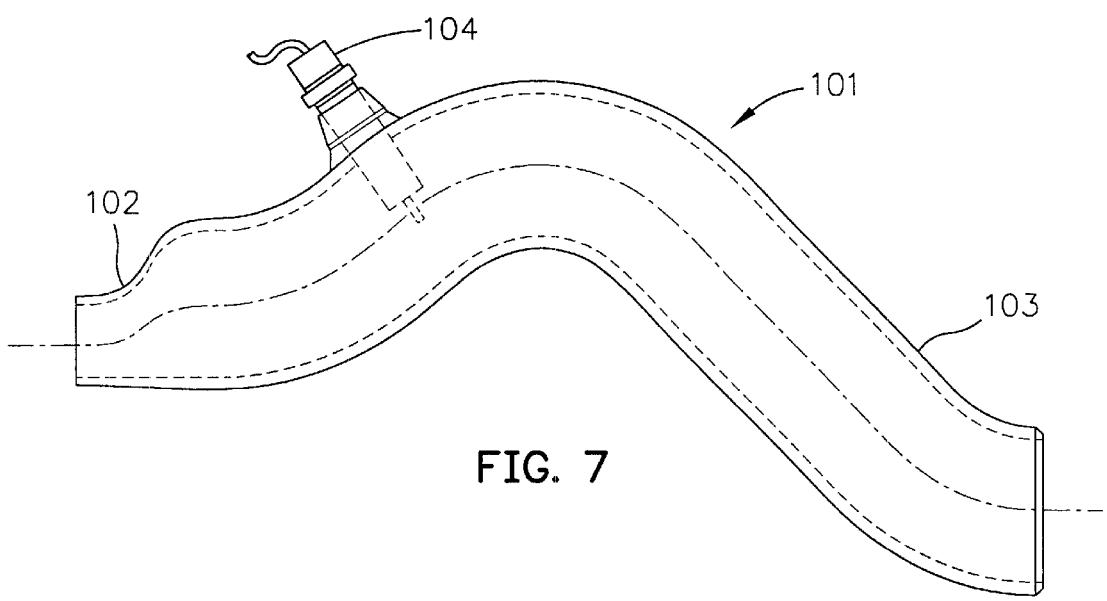
FIG. 7 is a side view of yet another alternative embodiment of the FIG. 1 flow conditioner, combining the structures of FIGS. 5 and 6.

The FIG. 7 flow conditioner 101 combines the functional attributes of FIGS. 6 and 5B with inlet expansion 102 to enable sensor 104 to monitor high flow rates, and with outlet arm 103 lengthened to accommodate the situation where the downstream conduit does not have a downward turn near the flow conditioner outlet.

In each of the embodiments of FIGS. 5 through 7 the sensor is shown mounted in the top position on the flow conditioner. It could equally be mounted on the side for each embodiment, as shown in the example of FIG. 2.

Although the above description discusses the use of an intrusive type of sensor, non-intrusive types of sensors could also be used for detecting the height of the liquid level above the reference plane, as well as the gas or liquid flow rate through the pipe segment.

Figure 8:
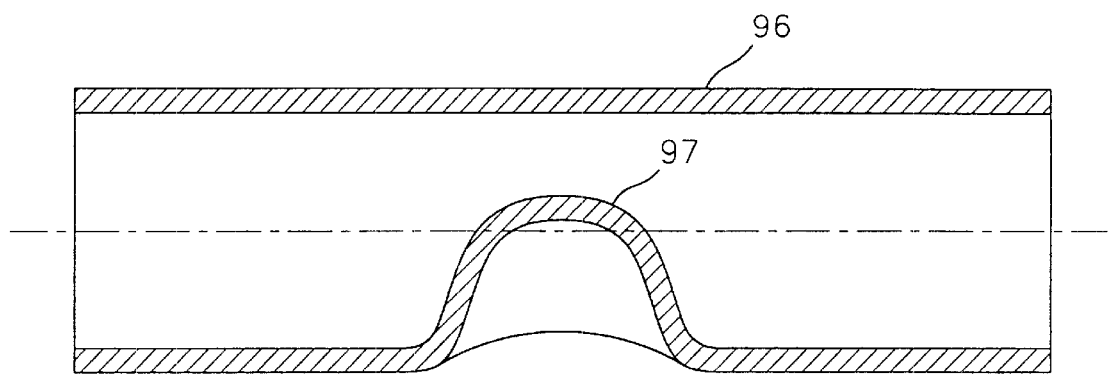
FIG. 8 is a side view of still another embodiment of the FIG. 1 flow conditioner.

Other flow conditioner configurations are also possible. The preferred pipe segment is shown as having a reverse-bend in FIGS. 1 and 2, but as shown in FIG. 8, a straight pipe segment 96 could be formed with bump or dimple 97 creating the weir.

In view of the above description, it is likely that those skilled in the art will envision modifications and improvements to this invention. The invention is limited only by the spirit and scope of the accompanying claims, with due consideration being given to a reasonable range of equivalents.

What is claimed is:

1. A liquid/gas phase detector system comprising:
    a flow conditioner comprised of a segment of pipe having a wall, an inlet end and an outlet end;
    an elevated surface creating a weir within said pipe segment that is between said inlet and outlet ends, said weir having a crest, said crest of said weir being vertically higher than the centerline of said inlet end, a reference plane being defined as a horizontal extension toward said inlet end from said crest of said weir;
    a sensor configured to effectively extend through said wall of said pipe segment at a location between said inlet end and said crest, said sensor having a sensing element with a sensitive portion and being so configured and mounted to said pipe segment that said sensitive portion of said sensing element is vertically higher than said reference plane, said sensor being configured to generate signals relative to pressure, flow and phase related changing events in said pipe segment; and
    means for conducting the signals to a location remote from said sensor for processing;
    whereby when liquid within said inlet end accumulates to a level higher than said reference plane, it will be detected by said sensor as it flows over said crest of said weir to said outlet end.

2. The detector system recited in claim 1, wherein said sensor extends through said wall of said pipe section on the upper surface thereof, said sensing element extending generally downwardly toward and short of said reference plane.

3. The detector system recited in claim 2, wherein said sensor comprises a reference sensing element and a heated sensing element.

4. The detector system recited in claim 2, wherein said sensitive portion of said sensing element is positioned between about ⅛ (0.125) inch and about 3/16 (0.1875) inch above said reference plane.

5. The detector system recited in claim 1, wherein said sensor extends laterally through said wall of said pipe section on one side thereof, said sensitive portion of said sensing element extending generally laterally toward and at all times positioned above said reference plane.

6. The detector system recited in claim 5, wherein said sensor comprises a reference sensing element and a heated sensing element.

7. The detector system recited in claim 5, wherein said sensitive portion of said sensing element is positioned between about ⅛ (0.125) inch and about 3/16 (0.1875) inch above said reference plane.

8. The detector system recited in claim 1, and further comprising a controller for converting the signals from said sensor to useful output indications.

9. The detector system recited in claim 1, and further comprising a coupling element on each end of said pipe segment for connecting said pipe segment to external conduits.

10. The detector system recited in claim 1, whereby said sensor generates a reference sensor signal and a heated sensor signal, the difference between them being the output of said sensor and having a first value when there is no fluid flow through said pipe segment, a second value when there is gas flow through said pipe segment, and third value when there is liquid flow through said pipe segment.

11. The detector system recited in claim 10, wherein said first signal changes with changes in the gas pressure within said pipe segment.

12. The detector system recited in claim 10, wherein said second signal changes with changes in gas flow rate through said pipe segment.

13. The detector system recited in claim 10, wherein said third signal changes with changes in liquid flow rate through said pipe segment.

14. The detector system recited in claim 1, and further comprising:
    a signal processor for converting the signals from said sensor to a different form; and
    an indicator coupled to said signal processor for converting the signals from said signal processor to human useful form.

15. The detector system recited in claim 1, wherein said inlet end and said outlet end of said pipe segment are generally horizontally axially aligned.

16. The detector system recited in claim 1, wherein said outlet end is lower than said inlet end.

17. The detector system recited in claim 16, wherein the interior open cross-section of said inlet end is smaller than the interior open cross-section of said pipe segment at the location of said sensor.

18. The detector system recited in claim 1, wherein the interior open cross-section of said inlet end is smaller than the interior open cross-section of said pipe segment at the location of said sensor.

19. The detector system recited in claim 1, wherein said crest of said weir is substantially above the entirety of said inlet end.

20. The detector system recited in claim 1, wherein the interior of said pipe segment has a generally inverted V-shaped configuration.

21. A fluid flow conditioner comprising:
a segment of pipe having a wall, an inlet end and an outlet end;
an elevated surface creating a weir within said pipe segment that is between said inlet and outlet ends, said weir having a crest, said crest of said weir being vertically higher than the centerline of said inlet end, a reference plane being defined as a horizontal extension toward said inlet end from said crest of said weir;
a sensor configured to effectively extend through said wall of said pipe segment at a location between said inlet end and said crest, said sensor having a sensing element with a sensitive portion and being so configured and mounted to said pipe segment that said sensitive portion of said sensing element is vertically higher than said reference plane, said sensor being configured to generate signals relative to pressure, flow and phase related changing events in said pipe segment; and
means for conducting the signals to a location remote from said sensor for processing; and
a controller for converting the signals from said sensor to useful output indications;
whereby when liquid within said inlet end accumulates to a level higher than said reference plane, it will be detected by said sensor as it flows over said weir to said outlet end.

22. The flow conditioner recited in claim 21, wherein said inlet end and said outlet end of said pipe segment are generally horizontally axially aligned.

23. The flow conditioner recited in claim 21, and further comprising a coupling element on each end of said pipe segment for connecting said pipe segment to external conduits.

24. The flow conditioner recited in claim 21, wherein said outlet end is lower than said inlet end.

25. The flow conditioner recited in claim 24, wherein the interior open cross-section of said inlet end is smaller than the interior open cross-section of said pipe segment at the location of said sensor.

26. The flow conditioner recited in claim 21, wherein the interior open cross-section of said inlet end is smaller than the interior open cross-section of said pipe segment at the location of said sensor.

27. The flow conditioner recited in claim 21, wherein said crest of said weir is substantially above the entirety of said inlet end.

28. The flow conditioner recited in claim 21, wherein the interior of said pipe segment has a generally inverted V-shaped configuration.

29. A fluid flow conditioner comprising:
a segment of pipe having a wall, an inlet end and an outlet end, said inlet end and said outlet end being horizontally axially aligned;
an elevated surface creating a weir within said pipe segment that is between said inlet and outlet ends, said weir having a crest, said crest being vertically higher than the centerline of said inlet and outlet ends, a reference plane being defined as a horizontal extension toward said inlet end from said crest of said weir;
a sensor extending through the wall of said pipe segment at a location between said inlet end and said crest, said sensor having sensing means extending to a location within said pipe segment which is vertically higher than said reference plane, said sensing means being configured to generate a signal relative to the changing events in said pipe segment;
means for conducting the signals to a location remote from said sensor for processing; and
a controller for converting the signals from said sensor to useful output indications;
whereby when liquid within said inlet end accumulates to a level higher than said reference plane, it will be detected by said sensor as it flows over said weir to said outlet end.

30. A liquid/gas phase detector system system comprising:
a flow conditioner comprised of a segment of pipe having a wall, an inlet end and an outlet end;
an elevated surface creating a weir within said pipe segment that is between said inlet and outlet ends, said weir having a crest, said crest of said weir being vertically higher than the centerline of said inlet end, a reference plane being defined as a horizontal extension toward said inlet end from said crest of said weir;
sensor means configured to effectively extend through said wall of said pipe segment at a location between said inlet end and said crest, said sensor means having a sensing means which is vertically higher than said reference plane, said sensor means being configured to generate signals relative to pressure, flow and phase related changing events in said pipe segment; and
means for conducting the signals to a location remote from said sensor means for processing;
whereby when liquid within said inlet end accumulates to a level higher than said reference plane, it will be detected by said sensor means as it flows over said crest of said weir to said outlet end.

31. The detector system recited in claim 30, wherein said sensor means comprises a sensing element extending through said wall of said pipe section on the upper surface thereof, said sensing means extending generally downwardly toward and short of said reference plane.

32. The detector system recited in claim 30, wherein said sensor means comprises a sensing element extending laterally through said wall of said pipe section on one side thereof, said sensing means extending generally laterally toward and at all times positioned above said reference plane.

33. The detector system recited in claim 30, and further comprising controller means for converting the signals from said sensor means to human useful output indications.

34. The detector system recited in claim 30, and further comprising:
signal processor means for converting the signals from said sensor means to a different form; and
an indicator coupled to said signal processor means for converting the signals from said signal processor means to human useful form.

* * * * *